(12) United States Patent
Cox et al.

(10) Patent No.: US 7,717,826 B2
(45) Date of Patent: May 18, 2010

(54) ELECTRICAL SIGNATURE ANALYSIS TO QUANTIFY HUMAN AND ANIMAL PERFORMANCE ON FITNESS AND THERAPY EQUIPMENT SUCH AS A TREADMILL

(75) Inventors: Daryl F. Cox, Knoxville, TN (US); Charles D. Hochanadel, Oak Ridge, TN (US); Howard D. Haynes, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 11/688,893

(22) Filed: Mar. 21, 2007

(65) Prior Publication Data

US 2008/0234107 A1    Sep. 25, 2008

(51) Int. Cl.
*A63B 71/00* (2006.01)
*A61B 5/22* (2006.01)
*A61B 5/103* (2006.01)

(52) U.S. Cl. .................. 482/8; 73/379.04; 73/865.4; 600/587; 600/592

(58) Field of Classification Search .............. 482/1–9, 482/54; 600/587, 595; 73/865.4, 862.68, 73/116, 862.193, 379.04; 434/258; 235/105; 377/24.2; 702/160; 324/71.1, 76.11, 76.13
See application file for complete search history.

(56) References Cited

U.S. PATENT DOCUMENTS

| | | | | |
|---|---|---|---|---|
| 4,774,679 A * | 9/1988 | Carlin | .................. | 702/41 |
| 4,843,308 A * | 6/1989 | Frame | .................. | 324/120 |
| 5,299,454 A * | 4/1994 | Fuglewicz et al. | .................. | 73/172 |
| 5,310,392 A * | 5/1994 | Lo | .................. | 482/63 |
| 5,312,310 A * | 5/1994 | Shimizu et al. | .................. | 482/54 |
| 5,314,391 A * | 5/1994 | Potash et al. | .................. | 482/7 |
| 5,391,080 A * | 2/1995 | Bernacki et al. | .................. | 434/254 |
| 5,495,169 A * | 2/1996 | Smith | .................. | 324/127 |
| 5,938,565 A * | 8/1999 | Bernacki | .................. | 482/5 |
| 5,952,585 A * | 9/1999 | Trantzas et al. | .................. | 73/862.046 |
| 6,273,863 B1 | 8/2001 | Avni et al. | | |
| 6,575,878 B1 * | 6/2003 | Choy | .................. | 482/54 |
| 6,645,126 B1 * | 11/2003 | Martin et al. | .................. | 482/54 |
| 6,997,882 B1 | 2/2006 | Parker et al. | | |
| 7,231,834 B2 * | 6/2007 | Kurono | .................. | 73/800 |
| 2003/0055362 A1 * | 3/2003 | Hampton | .................. | 600/595 |
| 2006/0046909 A1 * | 3/2006 | Rastegar et al. | .................. | 482/91 |
| 2006/0052728 A1 * | 3/2006 | Kerrigan et al. | .................. | 600/595 |
| 2006/0082944 A1 * | 4/2006 | Koyanagi et al. | .................. | 361/93.1 |
| 2006/0189902 A1 * | 8/2006 | Takai et al. | .................. | 600/595 |
| 2006/0229162 A1 * | 10/2006 | Choy | .................. | 482/4 |
| 2006/0258915 A1 * | 11/2006 | Ueda et al. | .................. | 600/301 |

* cited by examiner

*Primary Examiner*—Nicholas D Lucchesi
*Assistant Examiner*—Sundhara M Ganesan
(74) *Attorney, Agent, or Firm*—Luedeka, Neely & Graham, P.C.

(57) ABSTRACT

The invention is a human and animal performance data acquisition, analysis, and diagnostic system for fitness and therapy devices having an interface box removably disposed on incoming power wiring to a fitness and therapy device, at least one current transducer removably disposed on said interface box for sensing current signals to said fitness and therapy device, and a means for analyzing, displaying, and reporting said current signals to determine human and animal performance on said device using measurable parameters.

4 Claims, 13 Drawing Sheets

ELECTRICAL SIGNATURE ANALYSIS TO QUANTIFY HUMAN AND ANIMAL PERFORMANCE ON FITNESS AND THERAPY EQUIPMENT SUCH AS A TREADMILL

STATEMENT REGARDING FEDERALLY SPONSORED RESEARCH

This invention was made with United States Government support under Contract No. DE-AC05-00OR22725 between the United States Department of Energy and U.T. Battelle, LLC. The United States Government has certain rights in this invention.

BACKGROUND OF THE INVENTION

Gait analysis usually involves the measurement and interpretation of sequential events that occur in the gait cycle. The gait cycle includes all of the events occurring from one heel strike to the repeated heel strike of the same foot. Essential gait measurement parameters include space, time, and compressive forces. These measurements must be accurate, reproducible and related in time to be of value. Additional value results from real time data analysis to allow training for gait style modification, or adjustments of gait devices like shoes or braces.

Various types and methods of gait analysis exist today ranging from measured distances and a stopwatch to computerized 3-D video gait analysis systems. The cost, utility and efficacy of each system may limit their application in various settings. The Electrical Signature Analysis (ESA) system described herein provides a highly objective, comprehensive gait performance analysis.

BRIEF SUMMARY OF THE INVENTION

The invention is a human and animal performance data acquisition, analysis, and diagnostic system for fitness and therapy devices having an interface box removably disposed on incoming power wiring to a fitness and therapy device, at least one current transducer removably disposed on said interface box for sensing current signals to said fitness and therapy device, and a means for analyzing, displaying, and reporting said current signals to determine human and animal performance on said device using measurable parameters.

One unique and valuable aspect of the ESA system is its simple and direct ability to measure many of the fundamental characteristics of gait patterns using a standard treadmill. ESA requires no restrictive or sophisticated instrumentation and poses no risk to subjects other than walking on the treadmill at comfortable speeds. The system has an excellent market potential for demonstrating gait aberrations in rehabilitation settings, sports performance for coaches and athletes, and gait enhancements for footwear manufacturers.

ESA can be used to monitor physical condition and performance of human and animals. ESA has long been used as a tool for monitoring the condition and performance of pumps, valves and other electromechanical machinery, but has never been applied as a tool for analyzing human and animal condition and quantifying performance.

To further investigate this concept, electric voltage and current signals were recorded from an AC-powered treadmill as a person walked on the treadmill normally and in several irregular ways that simulated various physical impairments. The variations in walking styles produced many noticeable changes in the treadmill's electrical signatures, and demonstrated this new approach for sensing and measuring variations in human and animal physical condition. These results can serve as a foundation for further development of ESA-based methods and ultimately lead to the creation of new tools for measuring the physical rehabilitation progress of people recovering from injuries and surgeries that alter flexibility, mobility, strength, and balance.

DETAILED DESCRIPTION OF THE INVENTION

Figure 1:
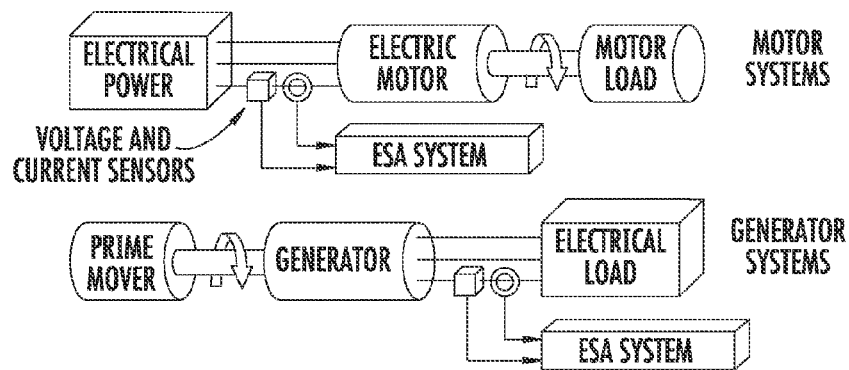
FIG. 1 is a schematic of the general method of electrical signature analysis.
Figure 2:
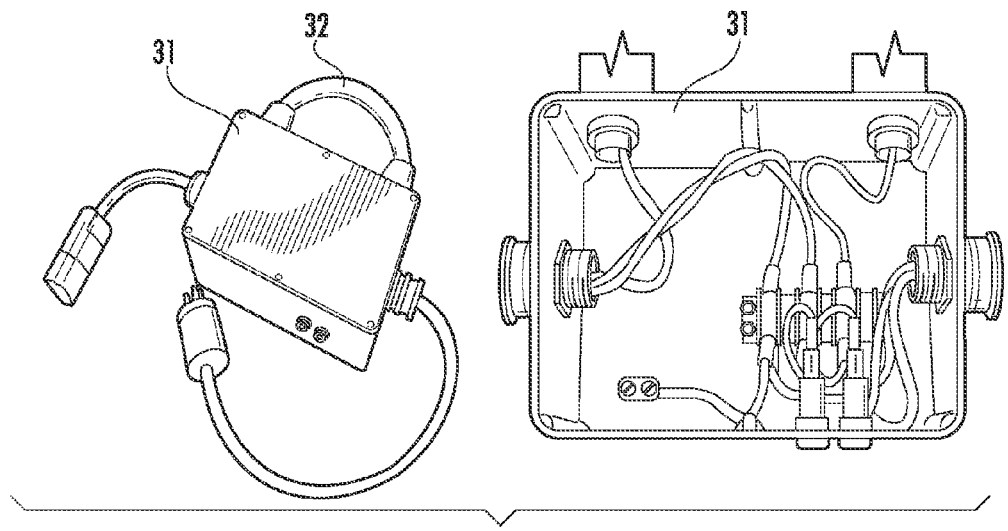
FIG. 2 is a photograph of the electrical interface box to a treadmill power source.

This invention is a device and method for detecting and monitoring physical condition and performance of humans and animals. It exploits the treadmill's and other electromechanical device's electric motor as a transducer for sensing load variations caused by a person or animal walking on the treadmill, and is a variation of Electrical Signature Analysis (ESA) technologies that were initially developed for assessing the condition of electromechanical machinery.

Treadmill electric voltage and current signals were recorded as a person walked on the treadmill normally and in several irregular ways that simulated various physical impairments. Using current and voltage measurements enables a calculation of power which can be used as an additional analysis parameter. The variations in walking styles produced many noticeable changes in the treadmill's electrical signatures, thus demonstrating the sensitivity needed to perform human and animal gait analysis.

With further development, ESA-based instrumentation can be developed and combined with conventional treadmills and other electrically-powered health equipment to provide new inexpensive tools for monitoring and quantifying the physical rehabilitation progress of people recovering from injuries and surgeries that have affected their gait, flexibility, mobility, strength, and balance. Other than clinical settings, applications of the invention include biomechanics sports conditioning and rehabilitation, direct results measurement for reporting progress and billing support to medical insurance companies, racehorse training and rehabilitation, athletic shoe and orthotic design, and prosthetic research and design.

Gait analysis is essential in physical medicine and is a fundamental tool of the orthopedist, physical therapist, and orthotist/prosthetist. The ability to assess and correct inefficient or dysfunctional gait patterns is fundamental to sound clinical practice. Gait aberrations can result from pain, neurological disorders, and musculoskeletal impairments and can lead to premature joint wear, myotendinous pain and functional disability. Long term, gait disorders may result in permanent disability, loss of balance, loss of independence, and increased fall potential.

ESA gives clinicians a new analysis tool that can be used independently or with other gait analysis techniques to increase accuracy and objectivity of gait analysis. The physical therapist may use this technology to enhance gait efficiency and balance with a large variety of cases in geriatric populations, post-fracture or post-surgical cases, injured athletes, and general sprains or strains. The orthotist may use this technology to study the effects of various braces and orthoses. The prosthetist could study gait efficiency and use this technology to modify prosthesis to enhance the desired gait characteristics.

Beyond the realm of rehabilitation, ESA may prove to be very useful with analysis of athletic performance, particularly with runners. One could establish characteristic 'signatures' of elite runners with the ESA process and compare them with other developing runners. The developing athlete can learn to model, and then feel the differences with more efficient running motions using the ESA process. Coaches could use the process to train young runners and to analyze workouts in real time.

Athletic foot wear manufacturers may use the ESA process to study the effect of various shoe modifications with running performance, motion control for stability, and force attenuation. The ESA process could provide objective data for sport specific foot wear related to athletic performance.

The ESA technology was originally invented and developed as a tool for assessing the condition of a wide variety of military, industrial, and consumer electromechanical equipment. ESA can be used to detect equipment defects and degradation, and unwanted changes in process conditions. ESA is truly non-intrusive and does not interfere with the operation of the equipment being monitored.

FIG. 1 illustrates the general ESA method. Load and speed variations in electromechanical systems generally produce correlated variations in current and voltage. ESA analyzes these small perturbations and matches them to their source. The resulting time and frequency signatures reflect loads, stresses, and wear throughout the system and provide the basis for assessing the operational condition of the monitored equipment.

Many machines and electrical appliances have been designed to directly interact with human and animals. The manner in which the human and animal uses the appliance determines how hard the appliance must work, and how much electrical energy is required. For example, if a power saw is not used correctly, additional friction and binding can occur between the saw blade and the material being cut. This results in the saw motor having to work harder; which causes it to draw more current. When used correctly, the motor does not have to work as hard, and the electric current is lower. Thus, by measuring the magnitude of the electric current used by the saw, the manner in which the saw is being used is also measured.

Other examples of machines whose operations are affected by how they are used include treadmills, exercise bikes, elliptical machines, and other fitness equipment used in gyms and physical therapy centers. While these machines have been designed to promote physical fitness, their designs are inherently sensitive to the physical attributes, health, and abilities of the user. Like the saw example, it is believed that by obtaining the electrical signatures of these exercise devices as they are being used, certain signature features will be present that are indicative of the physical condition and abilities of the user. After identifying and correlating these features, they can be used to track improvement or degradation in the user's physical condition over time.

Figure 3:
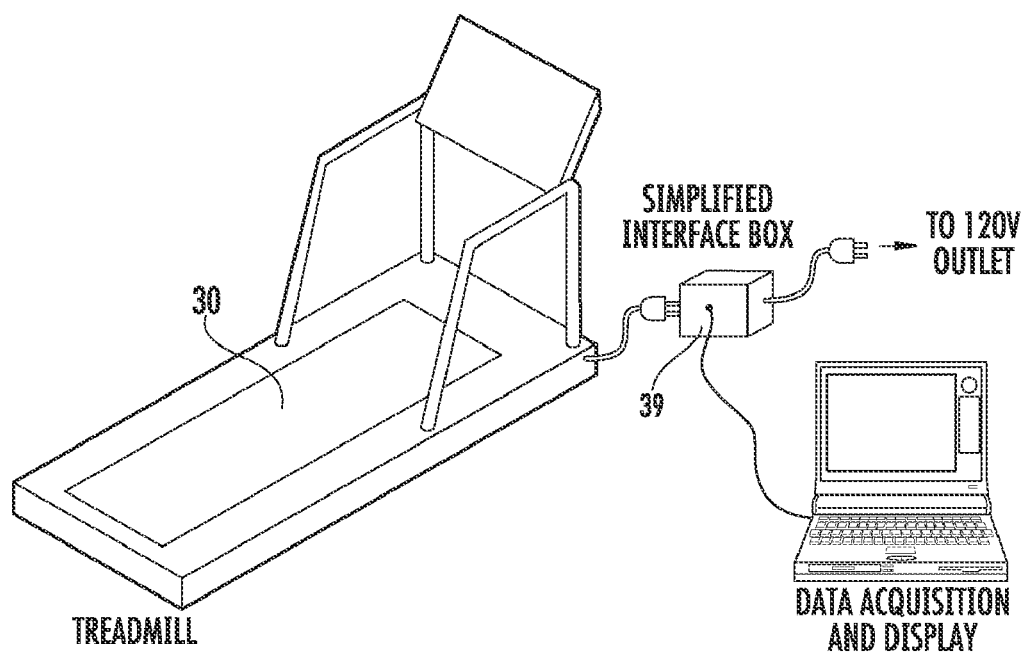
FIG. 3 is a schematic of a treadmill embodiment having a simplified interface box and a computer means for analyzing, displaying, and reporting the current signals.

FIG. 3 is a schematic of a treadmill embodiment having a simplified interface box and a computer means for analyzing, displaying, and reporting the current signals. The simplified interface box 39 includes a current transducer for obtaining current signals.

Figure 4:
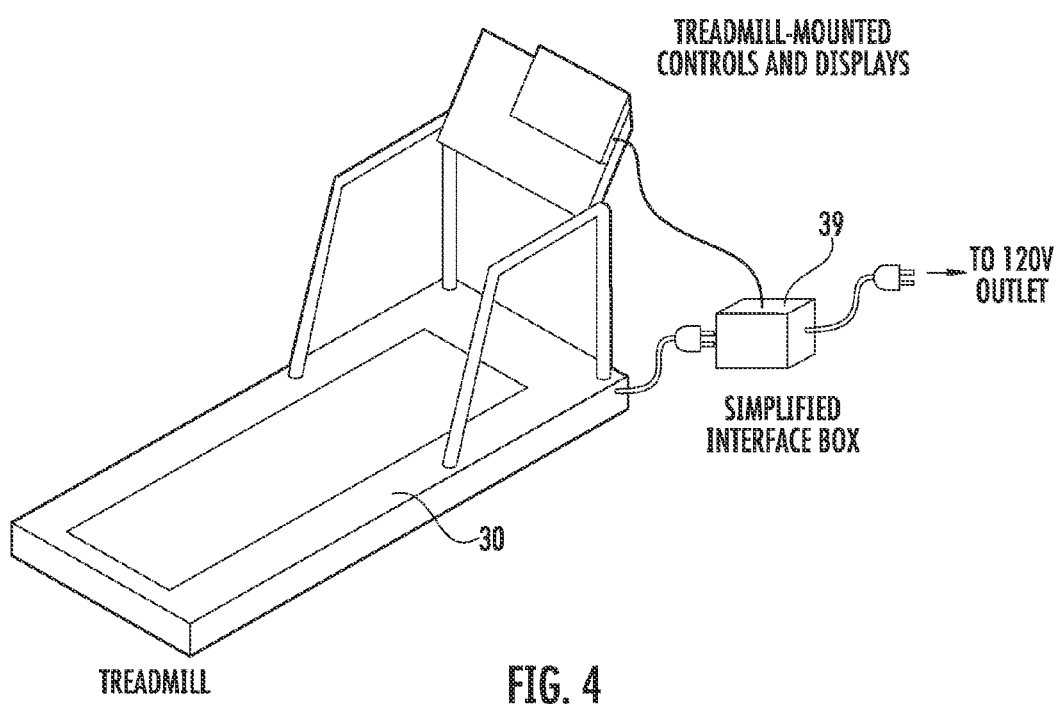
FIG. 4 is a schematic of a treadmill embodiment having a simplified interface box and an integrated treadmill means for analyzing, displaying, and reporting the current signals.

FIG. 4 is a schematic of a treadmill embodiment having a simplified interface box and an integrated treadmill means for analyzing, displaying, and reporting the current signals. The simplified interface box 39 includes a current transducer for obtaining current signals and the data is displayed on the treadmill stand itself. Other anticipated embodiments include a fully integrated treadmill wherein all components of the invention are built into the treadmill.

Figure 5:
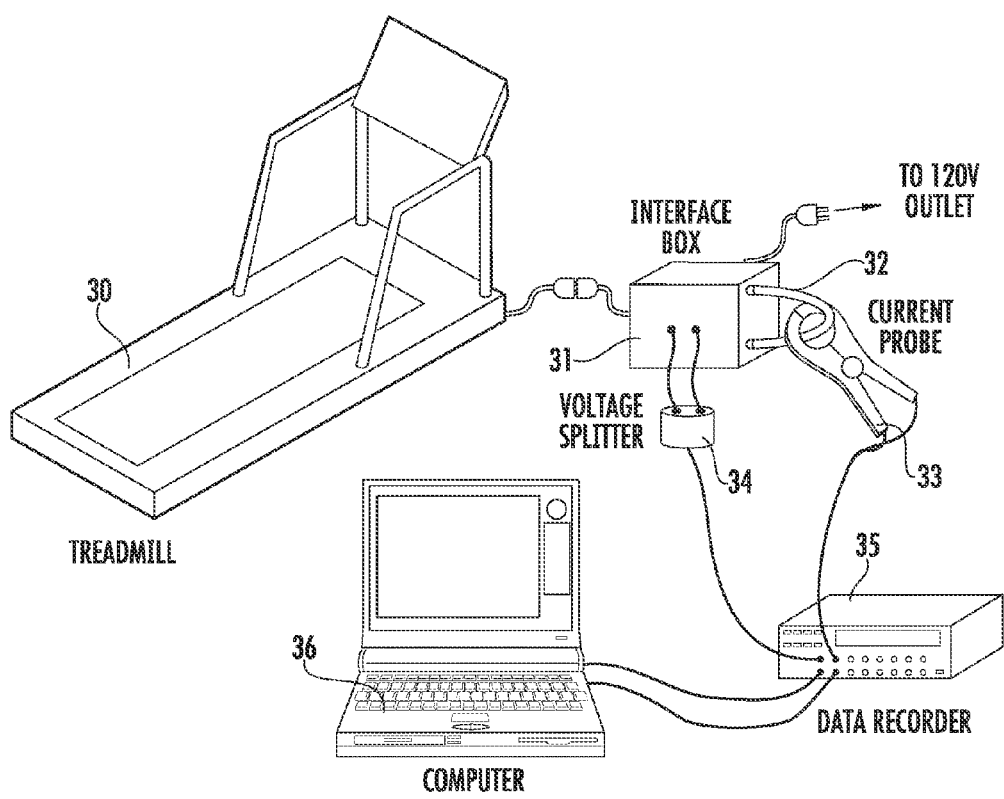
FIG. 5 is a schematic of the treadmill test setup.

In the test setup of FIG. 5, treadmill electrical signals were obtained using an electrical interface box 31 that was plugged into the treadmill 30 and then into a 120 V wall outlet. The interface box 31 contains an external loop 32 for accessing the treadmill electric current using a standard clamp-on current transducer 33. The interface box 31 also provides access to the full line voltage used by the treadmill 30. A 20:1 splitter 34 was then used to reduce the voltage levels so that they could be safely recorded on a data recorder 35. This interface box 31 makes it possible to easily and safely acquire electrical signals from any electrically powered exercise device such as a treadmill, an exercise bicycle, or an elliptical trainer.

FIG. 5 illustrates the general test setup. Electrical signals were obtained with a digital data recorder 35 and subsequently analyzed using a computer 36 and software that was specially developed for this application. Treadmill data were acquired under a variety of conditions. Table 1 summarizes the test conditions and walking styles that were recorded.

TABLE 1

| Date | Treadmill Speed (mph) | Treadmill Incline (%) | Walking Style |
| --- | --- | --- | --- |
| Nov. 17, 2005 | 4 | 0 | Normal walking |
| Nov. 17, 2005 | 4 | 5 | Normal walking |
| Nov. 17, 2005 | 4 | 10 | Normal walking |
| Nov. 22, 2005 | 3 | 0 | Normal walking |
| Nov. 22, 2005 | 3 | 0 | Walking, but with extended strides |
| Nov. 22, 2005 | 3 | 0 | Walking normal, but using the rails for support |
| Nov. 22, 2005 | 3 | 0 | Walking with a scissor gait |
| Nov. 22, 2005 | 3 | 0 | Walking with a sore toe |
| Nov. 22, 2005 | 3 | 0 | Walking with a stiff knee |
| Nov. 22, 2005 | 3 | 0 | Walking normally, but pointing toes out |
| Nov. 22, 2005 | 3 | 0 | Walking on toes only |
| Nov. 22, 2005 | 4 | 0 | Normal walking |
| Nov. 22, 2005 | 5 | 0 | Normal walking |

TABLE 1-continued

| Date | Treadmill Speed (mph) | Treadmill Incline (%) | Walking Style |
|---|---|---|---|
| Nov. 22, 2005 | 5 | 0 | Running |
| Dec. 2, 2005 | 3 | 0 | Normal walking with running shoes |
| Dec. 2, 2005 | 3 | 0 | Normal walking with no shoes |
| Dec. 2, 2005 | 3 | 0 | Normal walking with street shoes |
| Dec. 2, 2005 | 3 | 0 | Normal walking with taped ankle |
| Dec. 2, 2005 | 3 | 0 | Normal walking with taped ankle and toes |
| Dec. 2, 2005 | 3 | 0 | Normal walking with taped ankle and toes, and immobilized leg |
| Dec. 2, 2005 | 3 | 0 | Normal walking with taped ankle and toes, and restricted (taped) knee |
| Dec. 2, 2005 | 3 | 0 | Normal walking with restricted (taped) knee only |
| Dec. 2, 2005 | 3 | 0 | Normal walking while carrying 30 lbs of extra weight |

Treadmill voltage and current signals were recorded for all tests. To minimize variables, the same treadmill was used for all tests, and the same person served as the test subject for all tests. Several of these tests are further described later.

Figure 6:
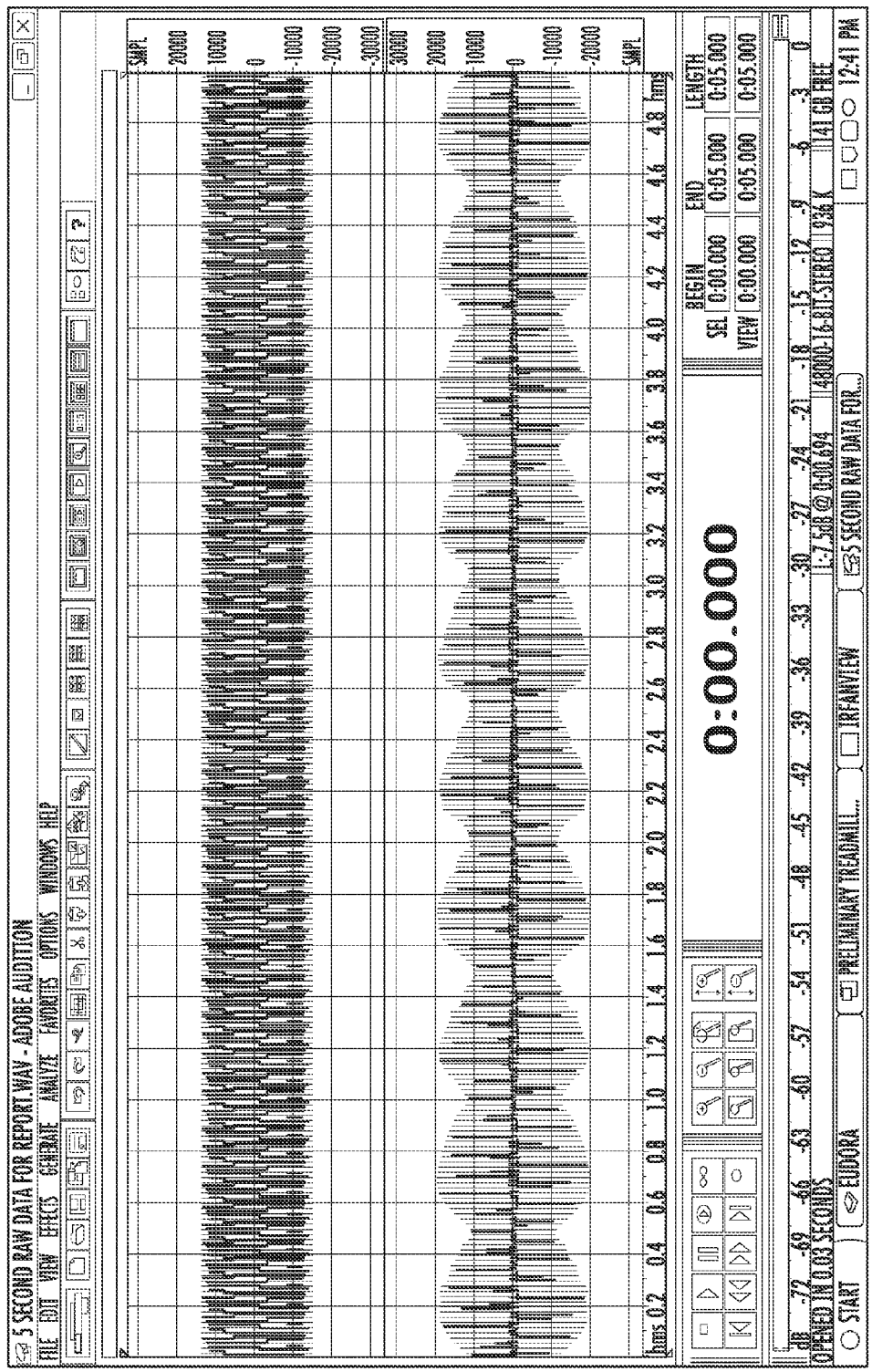
FIG. 6 is a graphical output of the voltage (top) and current (bottom) signals while a person is walking on a treadmill.
Figure 7A:
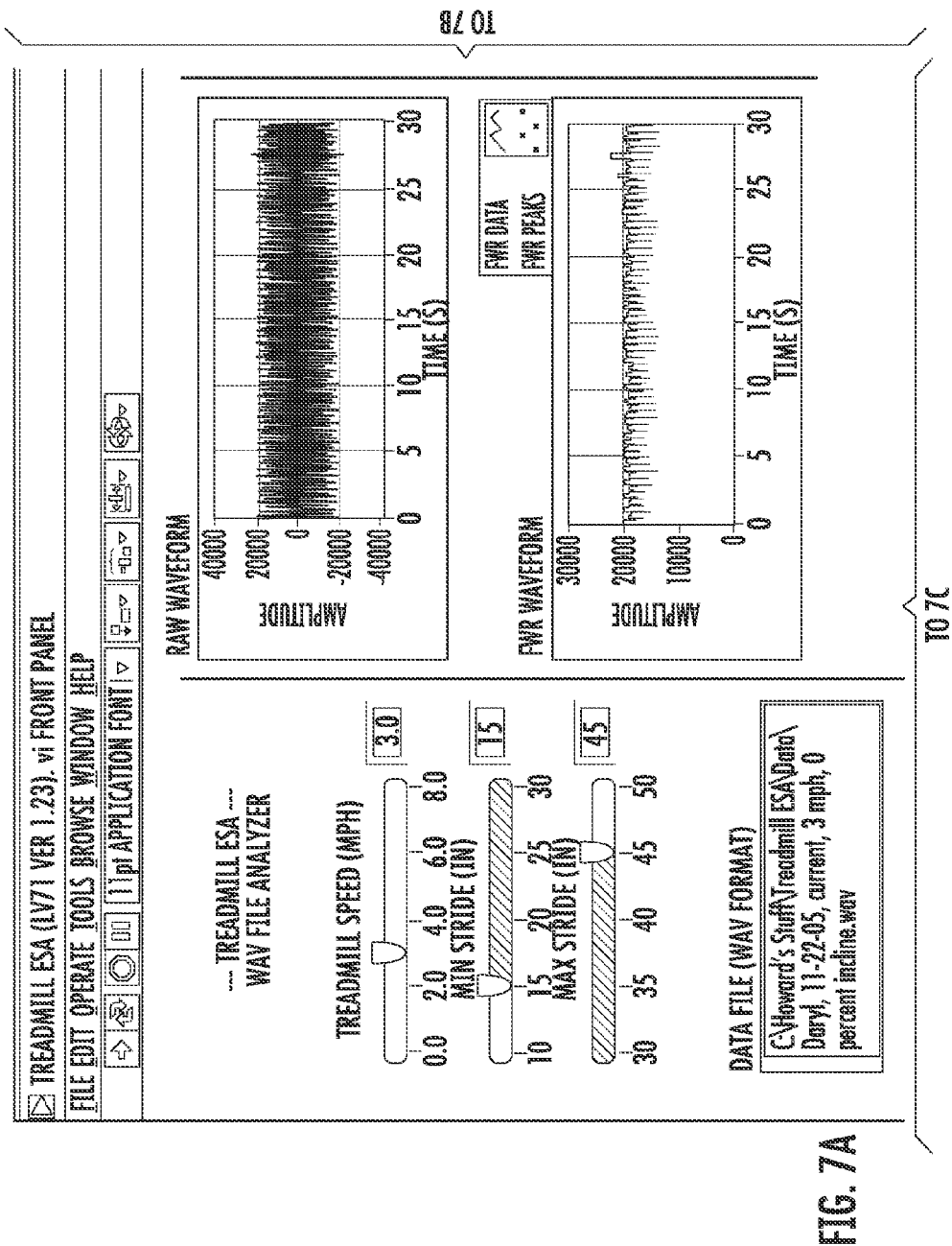
FIGS. 7A-7D are sample computer screens from the treadmill ESA software.
Figure 7B:
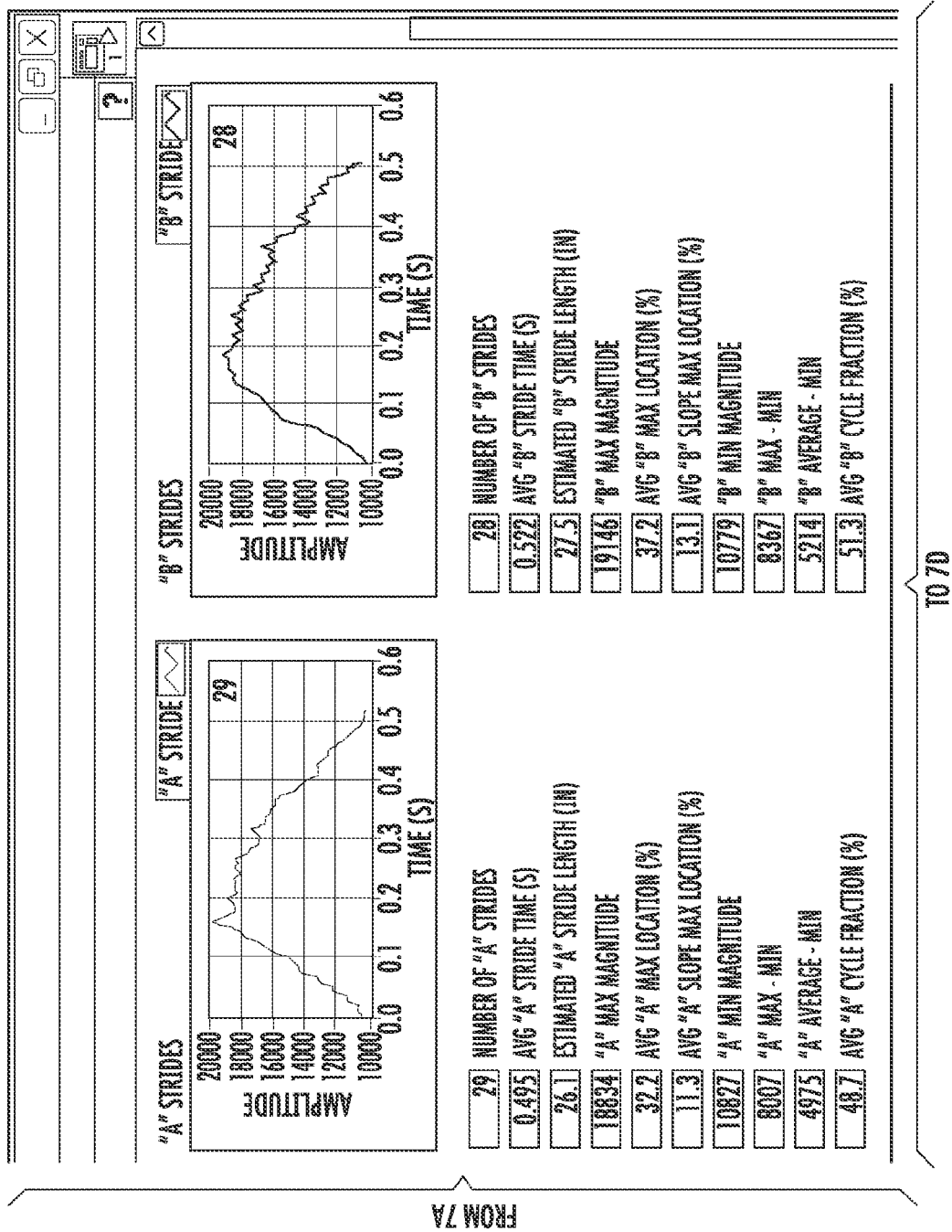
Figure 7C:
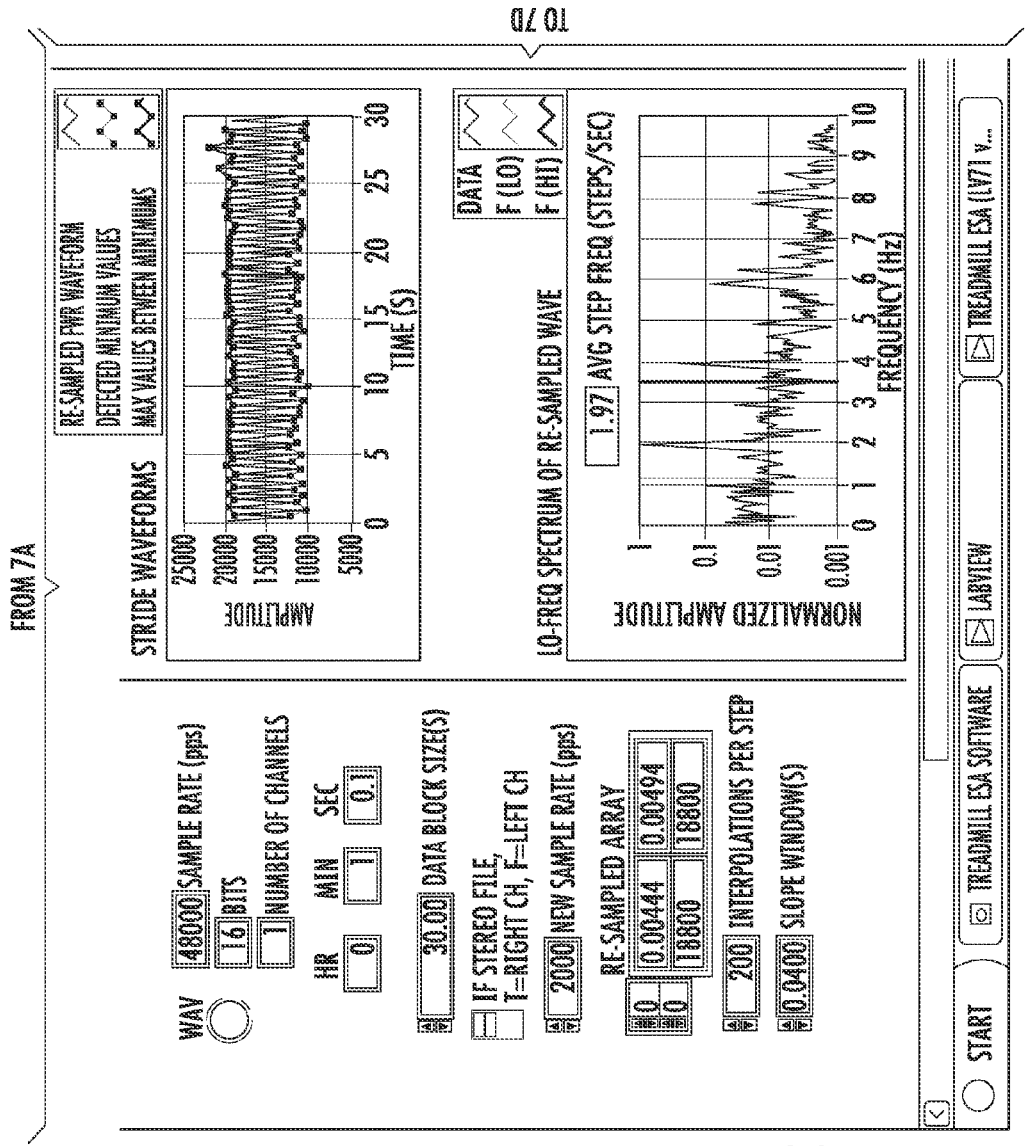
Figure 7D:
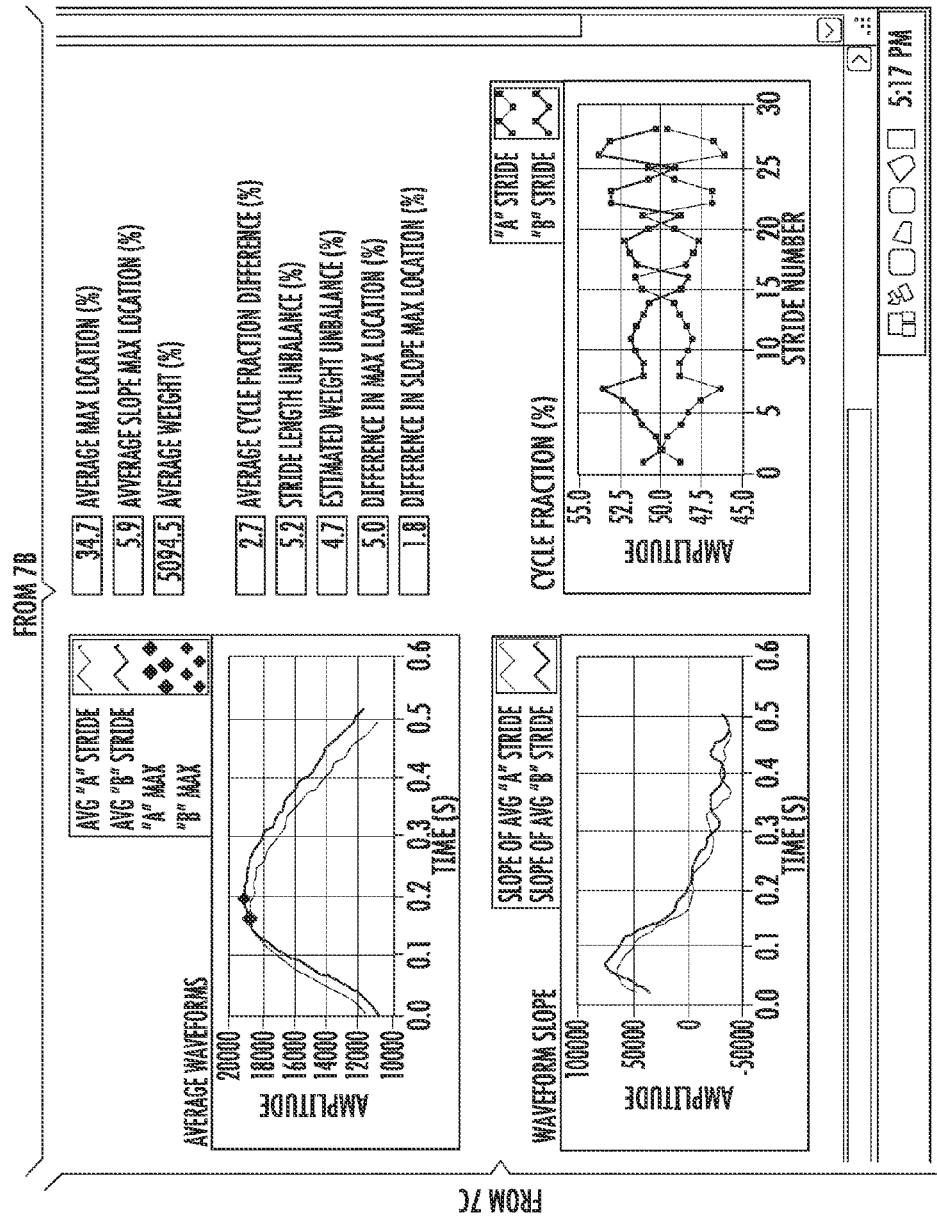

The recorded voltage and current signals were initially played back and examined using Adobe Audition, a commercially-available software package designed to record, edit, and play audio signals. As shown in FIG. 6, walking on the treadmill produced very little impact on the magnitude of the voltage signals, but produced dramatic variations in the magnitude of the electric current. For this reason, all additional analysis efforts focused on the current signals.

To analyze the electric current signals in more detail, a data analysis "virtual instrument" was developed using LabVIEW, a graphical data acquisition and analysis platform. The software controls and displays evolved as methods were identified to extract useful details (signatures) from the electric current data. Presently, the software is designed to apply a variety of ESA-based methods on treadmill electric current data that has been saved in the popular Windows sound file (WAV) format.

FIGS. 7A-7D illustrate sample screen information from the software, and shows (in the upper left corner of the screen) various controls that provide the ability to input the treadmill speed (in miles-per-hour) and a range within which the users stride falls. For the example, the data shown is taken from a test when the treadmill was operating at 3.0 miles per hour. The stride range of the user is selected to be between 15 and 45 inches.

Figure 8:
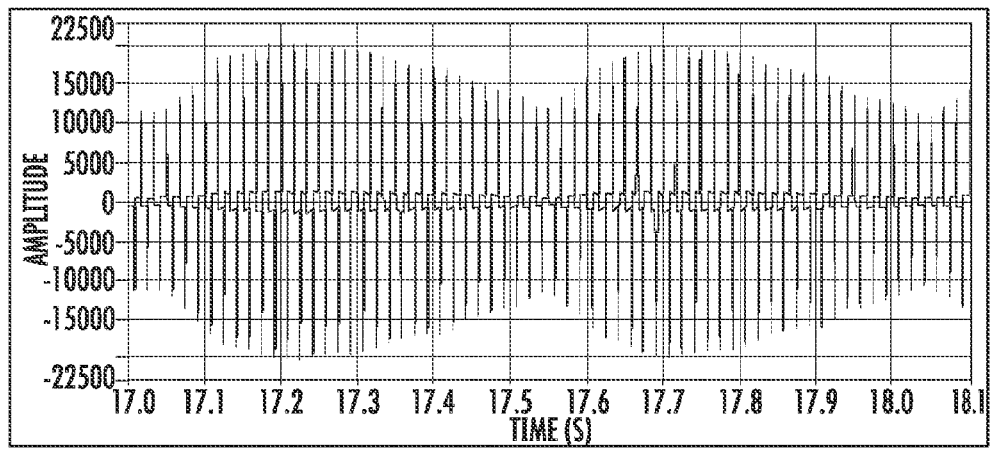
FIG. 8 is a graph showing the raw current waveform (top), full-wave rectified waveform with peaks identified (middle), and stride profile waveform constructed from rectified peaks (bottom).
Figure 8:
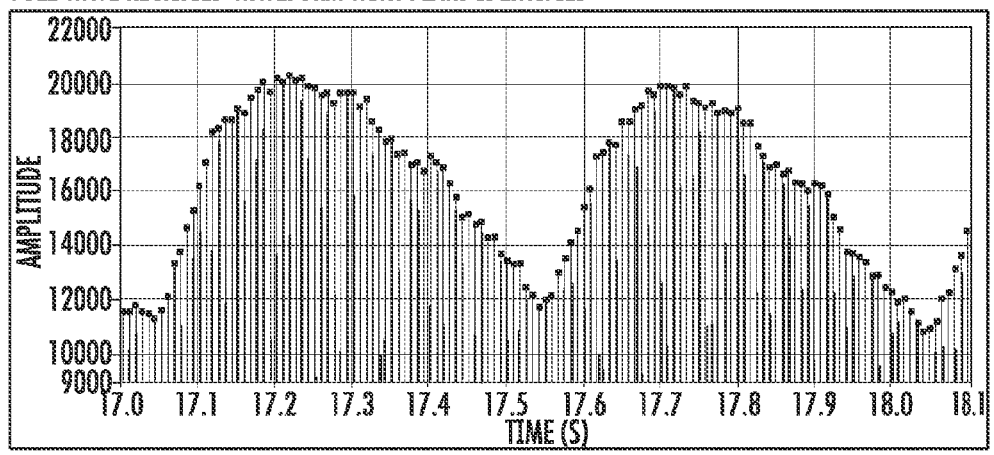
Figure 8:
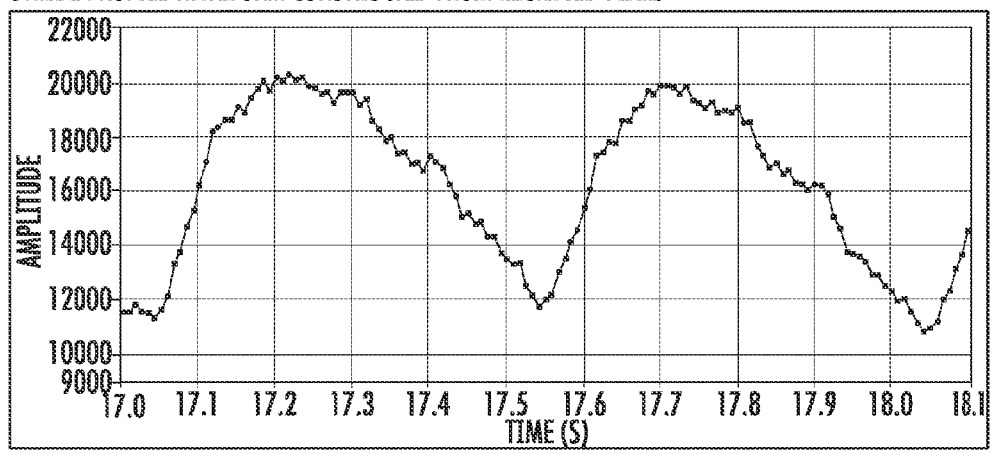

The software provides a tool for converting the "raw" electric current data into a revealing stride profile by first full-wave rectifying the current signal, and then using the rectified peaks to build the stride profile waveform. FIG. 8 illustrates this process where the software begins with "raw" data (top graph). After full-wave rectifying, the envelope peaks are automatically identified (middle graph) and used to construct the stride profile (bottom graph). This example shows the normal left-right stride signature of the user. The software then performs a frequency-analysis of the stride waveforms and calculates the overall stride frequency (in steps per second). The individual stride waveforms are then separated into two groups representing the left and right strides.

In order to identify which group is associated with which leg, the user consistently stepped on the treadmill first using his right foot. As this ESA-based system is further developed, a more positive method of identifying right from left is needed. One method of accomplishing this is to have the user wear a sensor on one leg that is preferably more sensitive only to one stride (e.g., their right) and transmit a signal to the data acquisition computer with each right step via a wireless link. The computer can then use this reference signal to positively identify the right stride waveform data from the left. Instruments such as foot switches are available which would positively identify left and right feet.

The load on the treadmill (and hence the current drawn by the treadmills motor) is sensitive to several factors, such as the weight of the user, the surface area of the belt that is in contact with the user, and the frictional losses between the treadmill mechanical surfaces. The software calculates an average stride profile, based on analyzing numerous stride waveforms and after accounting for the slight differences in the stride-to-stride durations in each leg. This averaging process is intended to "average out" the effects of the treadmill itself, since the user contacts a different section of the treadmill belt with each step. The average stride profiles are thus believed to be predominantly influenced by the gait of the user, and thus provide a suitable and sensitive signature for performing gait analysis.

Figures 9, 10:
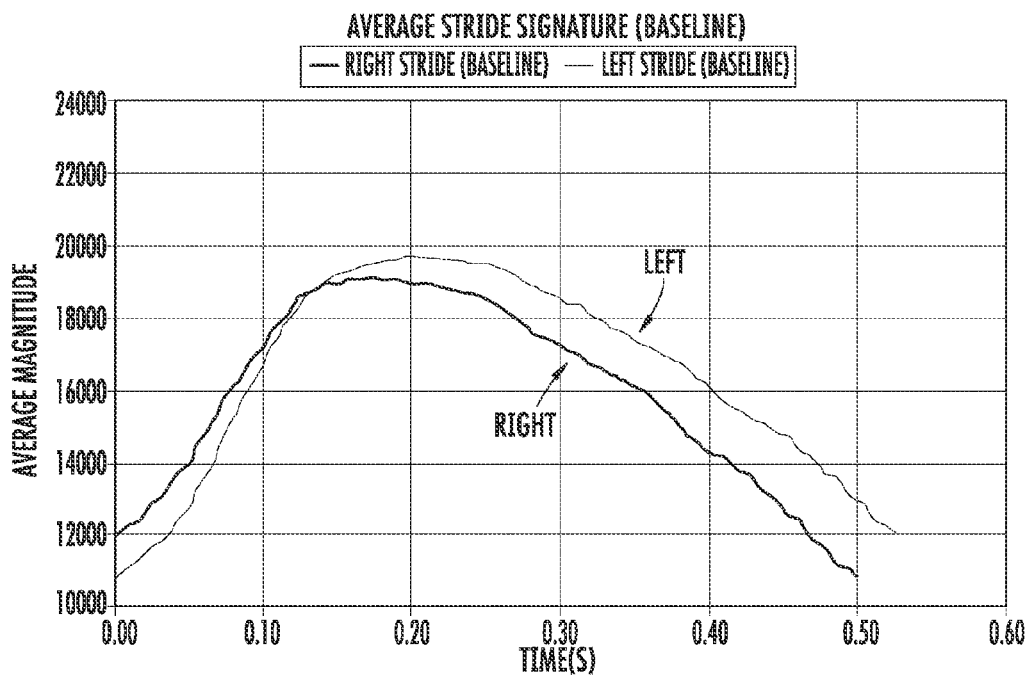
FIG. 9 is a graph showing the average stride profile for a user walking with a normal gait.
FIG. 10 is a sample output of measurable parameters from the "A" (right) and "B" (left) stride profiles.

Typical average stride profiles are shown in FIG. 9 for the user walking in a normal gait. As can be seen in the FIG. 9, differences exist between the right and left stride profile of the user. For example, the average left stride is characterized by a larger overall magnitude (thus indicating a larger load to the treadmill) and is about 5 percent longer in duration than the average right stride. The specific causes for the profile differences are not presently completely understood; however, they are repeatable and thus are believed to reflect user-specific conditions.

To better quantify the differences, the software also measures a variety of parameters that are present in the stride profiles. These parameter measurements are shown in FIG. 10. Several of these parameters were judged to be very sensitive indicators of gait anomalies such as stride profile, average stride profile, average cycle fraction difference, stride length unbalance, estimated weight unbalance, difference in max location, and difference in slope max location.

Average stride profiles are provided to illustrate the ability of ESA methods to characterize gait variations. The following "abnormal" conditions are presented; normal walking with additional weight, normal walking with taped right ankle, and taped right ankle and toes plus immobilized right leg.

Figure 11:
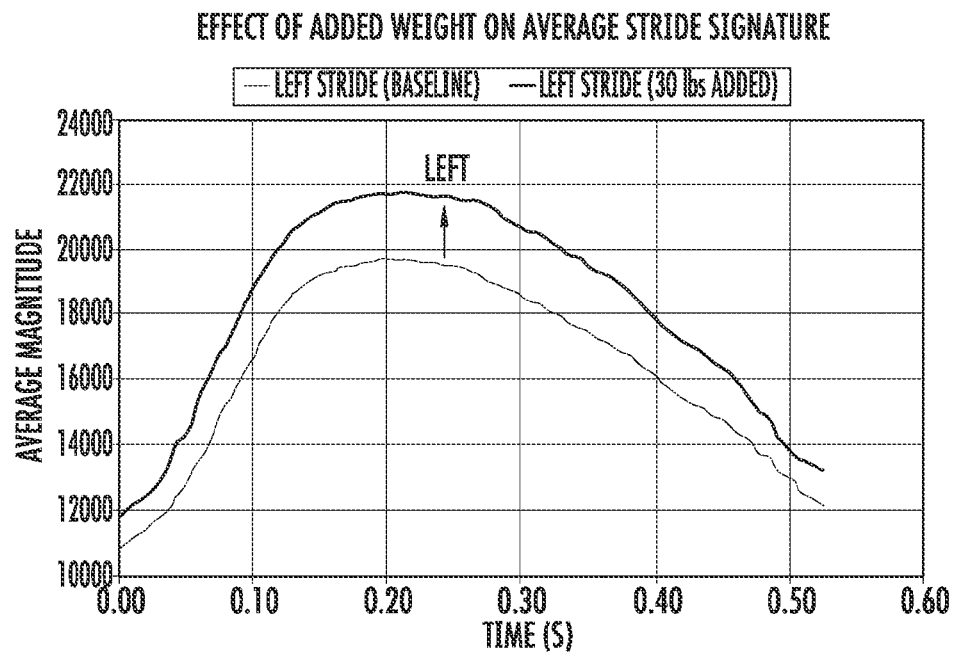
FIG. 11 is a graph showing the effect of added weight on an average left stride profile.
Figure 12:
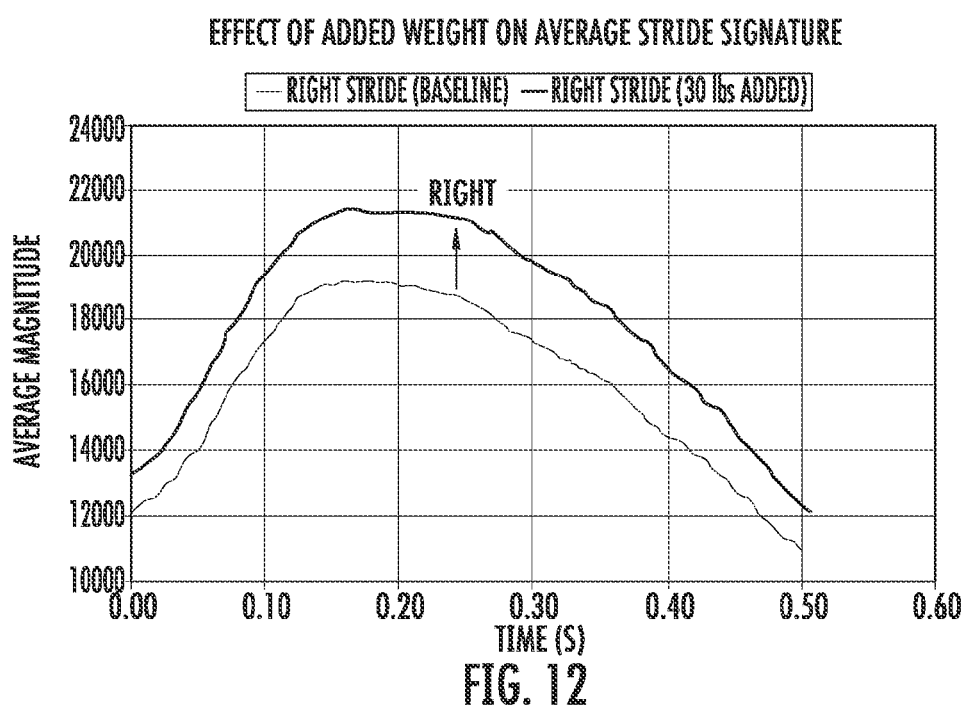
FIG. 12 is a graph showing the effect of added weight on an average right stride profile.

FIGS. 11 and 12 show the effect of the user carrying an additional 30 lbs while walking on the treadmill. When carrying the additional weight, the magnitudes associated with the right stride increased an average of 12.1 percent, and was relatively consistent throughout the entire stride. Similarly, the left side magnitudes increased an average of 11.0 percent. Since both right and left strides were affected approximately the same, the "balance" between the right and left strides was undisturbed.

Figure 13:
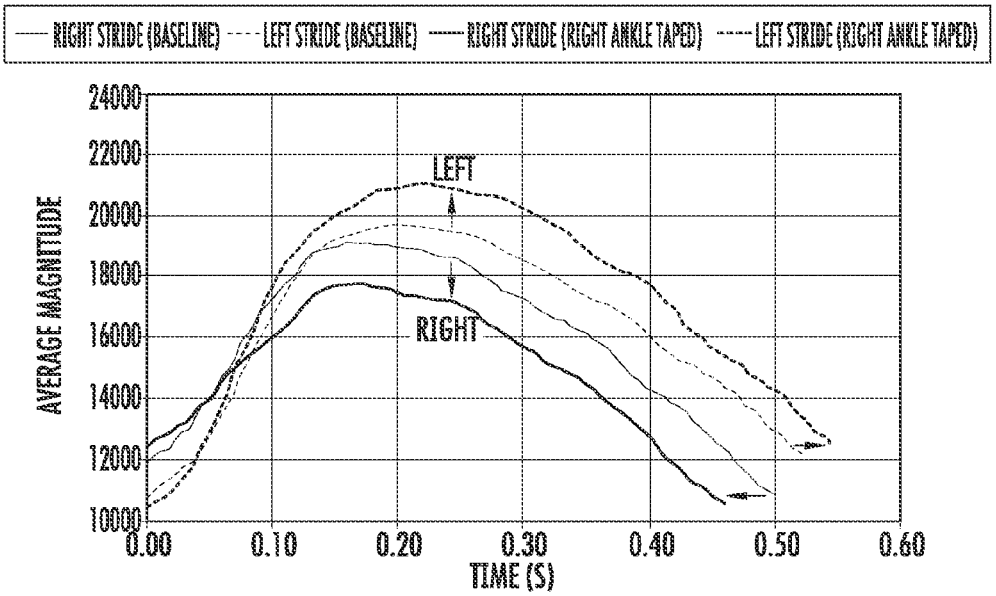
FIG. 13 is a graph showing the effect of a taped right ankle on the average stride profiles.

A test was performed after taping the user's right ankle. This removed the normal flexibility normally associated with the foot. When walking with a taped ankle, the balance between the two strides is significantly disturbed and is dramatically seen in the average stride profiles shown in FIG. 13. The right profile duration is noticeable shortened, and its magnitudes during the majority of the stride are significantly decreased. In contrast, the duration of the left profile increased, along with an increase in magnitudes throughout most of the stride. Thus, what is seen is a "spreading" of the two profiles as they move in opposite directions. This unbalance between the two strides is indicative of the differences in left and right strides, caused by the restricted movement of the right foot.

Figure 14:
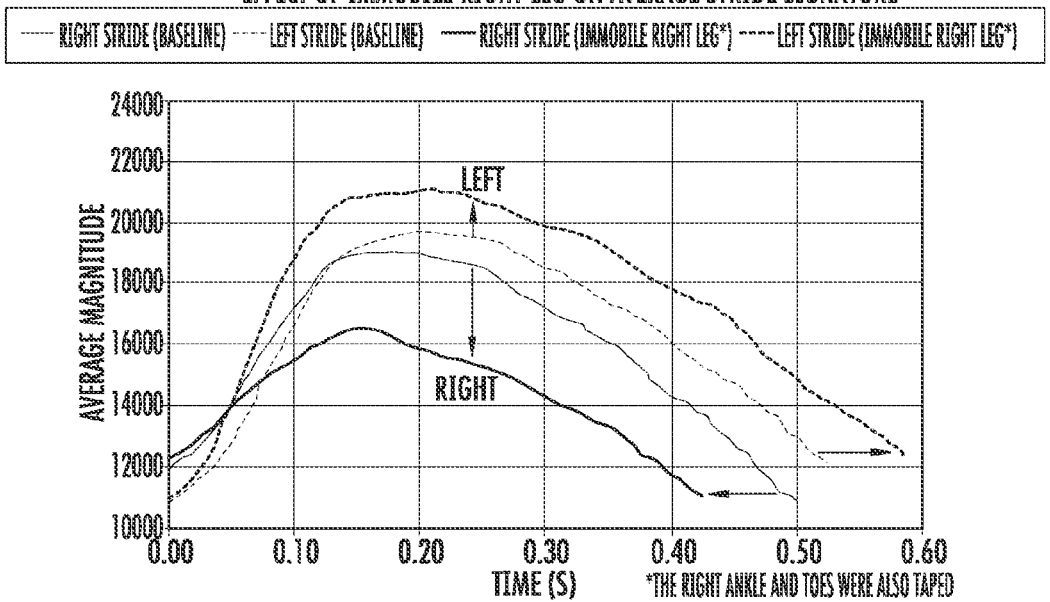
FIG. 14 is a graph showing the effect of an immobilized right leg on the average stride profiles.

A test was performed with several concurrent restrictions: the user's right toes and ankle were taped to prevent motion, and their right leg was immobilized by taping their knee. In this condition, the user walked on the treadmill, thus producing the average stride profiles shown in FIG. 14. The addition of the taped toes and immobilized leg to the already taped ankle further accentuated the unbalance between the two strides, as shown by the increased spreading between the left and right profiles. In this extreme case, the user spent only 42 percent of the time on their right foot, and 58 percent of the time on their left foot. The differences between the profile magnitudes were substantial. One method of quantifying the profile magnitudes is by measuring the average profile magnitudes and subtracting the minimum magnitude. In this manner, the average increase in treadmill running load associated with each stride is measured.

For the immobile leg case, the average profile magnitude minus the profile minimum for the compensating leg was 6525, which is almost double the magnitude of the right immobilized leg, which was 3344. This measure, along with the change in stride duration, and other measurable parameters are all indicative of the severe unbalance between the two strides, due to the imposed restrictions.

The average stride profiles that have been illustrated are only one way of visualizing and quantifying the treadmills electrical signature changes resulting from a person walking on it. The profiles themselves have many measurable characteristics that should correlate with known gait patterns.

Initial treadmill ESA tests were performed using a test subject who walked in various ways to simulate several foot and leg problems, including a "sore toe" and a "stiff knee." The 'sore-toe' and 'stiff knee' gaits represent common clinical gait patterns seen in rehabilitation. The sore-toe or antalgic gait is often seen in cases with pain problems related to the toes, foot or ankle. Examples might include a sprained ankle, bunion, turf toe, osteoarthritis, fracture, or other foot injury. Gait aberrations would be seen throughout the weight-bearing phase of the gait cycle from heel strike, through early, mid and late stance, as well as toe-off. The characteristic pattern is limited compressive loading, apropulsive toe-off, reduced stance time and reduced step and stride length on the affected side.

The 'stiff knee' gait would represent an individual who may have had surgery on the knee, wears a knee brace or immobilizer, has osteoarthritis of the hip or knee, or is post fracture and in a cast for immobilization. The characteristic gait abnormalities with the stiff knee are seen from mid-stance to toe-off and through the swing phase. These include reduced step and stride length, reduced swing time, circumduction of the hip to clear the foot, and limited toe-off and propulsion. The immobile extremity would have to be carried forward, which increases loads on the hip and the low back.

Normal gait can be divided into a stance phase, which takes roughly 60% of cycle time, and a swing phase, which takes 40% of the cycle time. Different gait abnormalities affect these phases of the gait pattern differently. The sore toe will want to minimize the time in compressive loading to protect the injured foot, where the stiff knee must be carried forward rather than being propelled forward. The resulting gait aberrations might reflect in the temporal, spatial and compressive measurements of the gait. The ESA process is sensitive to these gait patterns as well as being capable of identifying differences between normal left and right strides.

While there has been shown and described what are at present considered the preferred embodiments of the invention, it will be obvious to those skilled in the art that various changes and modifications can be made therein without departing from the scope.

We claim:

1. A method of analyzing a physical condition of a subject human or animal, comprising:
   sensing a waveform using a current sensor, the waveform representing an electrical current supplied to a fitness and therapy device;
   recording the waveform in a data acquisition device;
   rectifying the waveform;
   identifying in the rectified waveform a plurality of waveform peaks for each of a plurality of strides taken by the subject;
   using the plurality of waveform peaks per stride to construct a stride profile;
   using the stride profile to determine a first average stride signature and a second average stride signature that are representative of the subject's physical condition based on the stride profile.

2. The method of claim 1 further comprising associating the first average stride signature and the second average stride signature with right and left strides of the subject.

3. The method of claim 1 further comprising:
   performing a frequency analysis of at least one of the first average stride signature and the second average stride signature;
   calculating at least one stride frequency in steps per unit time for the at least one of the first average stride signature and the second average stride signature.

4. The method of claim 1 further comprising:
   performing a frequency analysis of the first average stride signature and the second average stride signature;
   calculating a first stride frequency in steps per unit time for the first average stride signature;
   calculating a second stride frequency in steps per unit time for the second average stride signature;
   calculating an average stride frequency difference between the first stride frequency and the second stride frequency.

* * * * *